(12) United States Patent
Weigand et al.

(10) Patent No.: US 9,108,046 B2
(45) Date of Patent: Aug. 18, 2015

(54) METHOD OF GENERATING AND/OR PROVIDING DATA FOR TISSUE TREATMENT

(75) Inventors: Frank Weigand, Heidenheim (DE); Frederik Wenz, Heidelberg (DE); Carsten Herskind, Besigheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 328 days.

(21) Appl. No.: 13/697,712

(22) PCT Filed: May 10, 2011

(86) PCT No.: PCT/EP2011/057518
§ 371 (c)(1),
(2), (4) Date: Nov. 13, 2012

(87) PCT Pub. No.: WO2011/141463
PCT Pub. Date: Nov. 17, 2011

(65) Prior Publication Data
US 2013/0058460 A1    Mar. 7, 2013

Related U.S. Application Data

(60) Provisional application No. 61/395,389, filed on May 12, 2010.

(30) Foreign Application Priority Data

May 12, 2010 (DE) ......................... 10 2010 020 352

(51) Int. Cl.
*A61N 5/10* (2006.01)
*A61N 5/01* (2006.01)
*A61B 6/00* (2006.01)

(52) U.S. Cl.
CPC ............ *A61N 5/1031* (2013.01); *A61N 5/1001* (2013.01); *A61N 5/1015* (2013.01); *A61N 5/1028* (2013.01)

(58) Field of Classification Search
USPC ........... 378/4, 5, 8, 10, 16, 19, 21, 29, 63–65, 378/87, 90, 97, 98.9, 101, 119, 140, 143, 378/162; 250/339.06, 339.07, 340, 341.1, 250/363.01, 369, 370.08, 370.09, 492.3, 250/493.1, 505.1; 699/3, 6, 7, 439, 443, 699/459, 467, 523
See application file for complete search history.

(56) References Cited

U.S. PATENT DOCUMENTS

| | | | |
|---|---|---|---|
| 6,494,835 B1 * | 12/2002 | Ciezki et al. | 600/439 |
| 8,148,703 B2 * | 4/2012 | Sommer | 250/493.1 |
| 2008/0049898 A1 | 2/2008 | Romesberg, III | |

FOREIGN PATENT DOCUMENTS

| | | |
|---|---|---|
| CN | 1260730 A | 7/2000 |
| DE | 102005056067 B3 | 6/2007 |
| JP | 2007526010 A | 9/2007 |
| WO | 2010011844 A1 | 1/2010 |

OTHER PUBLICATIONS

Waddington et al., "Assessment of effective dose from concomitant exposures required in verification of the target volume in radiotherapy," Br. J. Radiol., 77:577-61 (2004).

(Continued)

*Primary Examiner* — Bernard E Souw
(74) *Attorney, Agent, or Firm* — Kriegsman & Kriegsman

(57) ABSTRACT

A method of generating and/or providing data (28) for tissue treatment, in particular a tumor treatment, via a low-energy irradiation appliance (10) is described. Herein, the low-energy irradiation appliance (10) has a radiation source (14) for generating soft radiation, preferably of a radiation with a spectrum from 0 to a maximal radiation energy of 100 keV, in particular a radiation with a spectrum from 0 to a maximal radiation energy of 50 keV and an emitting device (15) for emitting the radiation to tissue, which is to be irradiated. The method is characterized by the following steps: physical data of the radiation source (14) is determined directly from leaving the emitting device (15); quality data of the tissue, for example the tumor tissue and/or the tissue (17) in the vicinity of the tumor, is determined; physical property data of the determined tissue is determined in connection with the radiation of the radiation source (14). Data (28) for the tissue treatment, for example the tumor treatment, is generated from the determined data and/or the determined data is provided for generating data for the tissue treatment, in particular tumor treatment.

10 Claims, 3 Drawing Sheets

(56) References Cited

OTHER PUBLICATIONS

Herskind et al., "Sphere of Equivalence—A Novel Target Volume Concept for Intraoperative Radiotherapy using Low-Energy X Rays," Int. J. Radiat. Oncol. Biol. Phys., 72(5):1575-81 (2008).

Haertl et al., "Praktische Dosimetrie and Konstanzpruefung zur Einfuehrung der intraoperativen Bestrahlung mit Intrabeam (Zeiss)," Z. Med. Phys., 19:288-93 (2009).

Office Action dated Feb. 3, 2011 from German Patent Office in connection with German Patent Application No. 10 2010 020 352.1.

\* cited by examiner

METHOD OF GENERATING AND/OR PROVIDING DATA FOR TISSUE TREATMENT

CROSS-REFERENCE TO RELATED APPLICATIONS

The present application is a 371 of International Application No. PCT/EP2011/057518, filed May 10, 2011, which claims the benefit of U.S. Provisional Patent Application No. 61/395,389, filed May 12, 2010.

BACKGROUND OF THE INVENTION

The present invention relates to a method of generating and/or providing data for tissue treatment, in particular for tumor treatment, by means of a radiation device.

Current methods of treating tumors provide for example, that the tumor is first excised by surgery and that the remaining edge tissue around the tumor is subsequently irradiated. It is also possible, that the tumor is fought by irradiation only without necessitating surgery.

When carrying out irradiation, it is crucial that the irradiation appliance is set in an appropriate manner, so that the required irradiation dose and irradiation intensity can be adjusted.

For example, DE 10 2004 039 191 A1 describes a solution, wherein for determination and monitoring of parameters of an irradiation therapy a first image of the tissue, which is to be irradiated, is generated in an image-providing medical technical method. By means of the first image a first parameter setting of the irradiation appliance is carried out. The tissue is irradiated with this parameter setting. In addition, at least one further image of the tissue, which is to be irradiated, is generated. Subsequently, an automatic comparison of the images is carried out and a signal is generated in case of deviations.

It is, for example, known to perform irradiations by means of so called high-energy linear accelerators. Therein the procedure of the planning of tumor irradiations with radiation therapy units, for example with x-ray therapy units, is as follows:

Firstly, an image, for example, a CT- or x-ray image, of a defined area around the tumor is generated in an image-providing method. This image is displayed on a display screen. Then the tumor and/or the tissue, which is to be irradiated, is marked. An irradiation plan is established, via a method, for example by means of appropriate software. To display the dose rate in the body of the patient to the surgeon directly on the image, the generated pictures are overlaid, for example by plotting isodose curves/surfaces/volumes, with values, which were calculated from the irradiation plan.

A disadvantage of this known solution is, that it is not applicable to low-energy irradiation appliances or irradiation methods, respectively. The procedure, which has been described in connection with irradiation via linear accelerator, cannot be used for low-energy systems and applications. Low-energy irradiation appliances are frequently being used in intraoperative methods.

In a system with considerably lower radiation energy, for example x-ray energy, than in systems with linear accelerators, the physical interactions of the low-energy rays with the tissue, which is to be irradiated, are considerably more complex due to the lower energy of the rays. This means, that different types of tissue weaken the rays to different degrees. This may be due to, for example, the so called photo- or Compton-effect. Furthermore, low-energy systems do not represent systems with monochromatic radiation quality. Low-energy systems rather show a very complex radiation spectrum from 0 to the current maximal radiation energy of for example 50 keV. That means, that with an increase in penetration of the radiation of the low-energy irradiation system into the tissue, the weakening even changes with homogenous tissue, as the radiation spectrum changes with increasing absorption in the tissue.

Therefore, the approach which is known in connection with linear accelerators cannot successfully be used with low-energy irradiation systems, as otherwise thereby large deviations of the calculations from the true value of the dose in the patient would occur.

SUMMARY OF THE INVENTION

The present invention is therefore based on the problem of providing a method of generating and/or providing data for tissue treatment via an irradiation method, wherein a direct, in particular visual, irradiation planning in connection with a low-energy irradiation appliance and/or a low-energy irradiation method can be performed.

This problem is solved by the method with the features according to independent patent claim 1 as well as by the computer program product with the features according to independent patent claim 10. Further features and details of the invention can be derived from the dependent claims as well as from the description. Features and details, which are described in connection with the method according to the invention, of course also apply in connection with the computer program product and vice versa.

The method according to the invention in particular provides a solution for a low-energy irradiation system or irradiation method, respectively, which allows for a direct, in particular visual, treatment planning. For example, such a system or method, respectively, may be used in an intraoperative method. Likewise, such a system or method, respectively, may be used for treatment of surfaces, for example outside of the body. But the invention is not limited to the mentioned possible applications.

Preferably, the system or method, respectively, according to the invention may be used in connection with tumor treatment. Likewise, usage, which is independent of a tumor surgery, may also be performed.

The low-energy irradiation system or low-energy irradiation method in particular represents a system or method, respectively, for radiotherapy of a tissue bed, for example a tumor bed. In such a method or with such a system, respectively, in particular after a resection, for example a resection of a tumor, the tissue bed, for example the tumor bed, is irradiated with soft rays, in particular X-rays. For that purpose, an emitting device of an irradiation source, which is preferably provided with an appropriate applicator of the correct size, is placed in the tissue bed, for example the tumor bed. With the low-energy application, the desired cell tissue can be irradiated directly, without having to irradiate through healthy tissue first.

According to the invention, a method of, in particular automatic, generating and/or providing of data for tissue treatment, in particular a tumor treatment, via a low-energy irradiation appliance is provided, wherein the low-energy irradiation appliance has an irradiation source for generating soft radiation, preferably radiation with a spectrum of 0 to a maximal radiation energy of 100 keV, in particular a radiation with a spectrum of 0 to a maximal radiation energy of 50 keV, and an emitting device for emitting the radiation to a tissue which is to be irradiated. The invention is not limited to a radiation source up to 100 kV, in particular 50 kV. The present invention is rather generally applicable for the soft radiation range, in particular the soft X-ray range.

The low-energy irradiation appliance thus firstly has a radiation source, which in operation generates radiation, for example X-radiation. The generated radiation is directed to the tissue, which is to be irradiated, via an appropriate emitting device. The emitting device may be arranged and/or formed directly at the radiation source or may be connected to the radiation source via a probe device. In general, also so called applicator equipment is used in the radiation appliance of the invention. Applicator equipment, for example, consists of an applicator element, which is designed for receiving the emitting device. That means, that the emitting device, possibly with the probe device, is inserted, for example pushed, into the applicator element. If applicator equipment is being used, the applicator equipment may, for example, be the emitting device.

In particular, the emitting device may be defined such, that it is a device, via which or from which, as the case may be, the radiation is emitted from the irradiation appliance to the tissue which is to be irradiated.

The method according to the invention is characterized by the following steps:
- physical data of the radiation source is determined directly from leaving the emitting device;
- quality data of the tissue, for example the tumor tissue and/or the tissue in the vicinity of the tumor, is determined;
- physical property data of the determined tissue in connection with the radiation of the radiation source is determined;
- data for the tissue treatment, for example the tumor treatment, is generated from the determined data and/or the determined data is provided for generating data for the tissue treatment, in particular the tumor treatment.

The method according to the invention is not limited to a specific course scheme, in particular of the first three method steps. It is merely important, that the respective data is determined and is subsequently further processed.

Preferably, the method according to the invention is carried out with support of computer(s). Thus, in that case at least one processing device and/or at least one data processing device is preferably provided, on which the method is carried out.

According to the method according to the invention, physical data of the radiation source is determined directly from leaving the emitting device. In particular, those physical data is determined at a location or in the area or vicinity of a location, where the radiation of said radiation source leaves the emitting device. In particular physical data are such data which physically describe and/or characterise the radiation source and/or the radiation being delivered or emitted from said radiation source. For example, it may be provided, that the spectrum of the radiation source is determined directly from leaving the emitting device as physical data of the radiation source. For example, the spectrum of the radiation source directly from leaving the tip of the probe element or the applicator equipment, respectively, may be determined. The values of the spectrum or of the spectra may preferably be generated by appropriate measurements, the results of which are advantageously stored in a file or data base. For example, also so called Monte-Carlo-calculations can be envisioned, which ab initio calculate and/or simulate the emitting characteristics of the x-ray source. The file and/or data base is preferably stored in a storage device, which the method or the processing unit, whereon the method is carried out, as the case may be, accesses or may access.

Furthermore, according to the method of the invention, quality data of the tissue, for example of the tumor tissue and/or of the tissue in the vicinity of the tumor, is determined. In particular, quality data are such data which provide information relating to the quality and/or nature and/or constitution and/or appearance and/or character and/or composition and/or consistence and/or configuration and/or texture and the like of the tissue. For example, it may be provided, that the quality data of the tissue, for example of the tumor tissue and/or of the tissue in the vicinity of the tumor, is determined by means of an image-providing method. For example, appropriate images may be generated, such as CT-images, roentgenogram, x-ray images and the like. To determine, preferably automatically determine, the tissue type, for example of the tumor tissue or of the tissue in the vicinity of the tumor, for example the images, for example CT-pictures or x-ray pictures, which were taken beforehand, may be used. It can be envisioned, that at each arbitrary spatial volume, the so called Voxel, in the vicinity of the tissue, for example in the vicinity of the tumor, the respective absorption at that location and thus the tissue type may be deducted from the respective gray value, preferably in Hounsfield-units. Therein, the term Voxel in particular denominates a data element in a three dimensional graphic. With the method according to the invention, first an image of the tissue, for example of the tumor tissue and/or of the tissue in the vicinity of the tumor, may for example be generated by means of the image providing method. The thus generated image will then preferably be analysed by means of an analysis method, for example with regards to the respective gray values. The tissue type will then be determined from the determined gray values and will be provided as or in terms of quality data. The connection between the gray value and the tissue type may, for example, be present as a data base or in a data base.

Furthermore, according to the method of the invention, physical property data of the tissue, which has been determined, is determined in connection with the radiation of the radiation source. Preferably, the mass-energy-absorption-coefficient will be determined as physical property data of the determined tissue is determined in connection with the radiation of the radiation source. Preferably, it is provided, that, if the respective mass-energy-absorption-coefficient in dependency of the energy $[\mu/\rho(E)]$ {tissue type} in the soft radiation range, for example X-ray range, is already known for different tissue types, these values are stored or are retrievable in the internet as a table in a file or database. If the respective mass-energy-absorption-coefficients in dependency of the energy $[\mu/\rho(E)]$ {tissue type} for specific tissue types are not yet know, these may be calculated with the help of the tissue consistency from the if the mass-energy-absorption-coefficient of the respective elements $[\mu/\rho(E)]$ {element} beforehand and may then be stored in this table. The file and/or data base is preferably stored in a storage device, which the method or the processing unit, whereon the method is carried out, as the case may be, accesses or may access. The values may thus be stored in the file or data base for future, in particular automatic, usage and/or calculation.

Subsequently, according to the method of the invention, data for the tissue treatment, for example for the tumor treatment, is generated from the determined data and/or the determined data is provided for generating data for the tissue treatment, for example the tumor treatment. Preferred but non-exclusive examples for this will be described in greater detail in the course of the description.

With the method according to the invention, it, in particular, becomes possible to indicate or display, respectively, the required data for planning a tissue treatment, for example a tumor treatment, with a low-energy irradiation system directly, in particular visually, in connection with quality data of the tissue, for example with CT-images or x-ray images. The method according to the invention thus, in particular, allows for the planning of a tissue treatment, for example a tumor treatment, by means of a low-energy radiation system with calculation and display of the physical and/or biological and/or medical effectiveness of the system.

Preferably, the dose rate for the tissue, which is to be irradiated, may be calculated, in particular automatically, from the determined data. If at a specific location within the tissue, the value of the dose rate, which reaches that location during the treatment, is required or desired, this can now easily be calculated with the method according to the invention, in particular, if the spectrum at the surface of the emitting device or the applicator device, is known. For example, the calculation of the absorbed dose rate at a specific point can be carried out from the radiation spectrum and from tissue type at this point.

In a preferred embodiment, the course of the calculation may be such that the connecting vector between the isocentre of the radiation emitting device and the point of the tissue, which is to be irradiated, is determined for calculating the dose rate; that the point of exit of the connecting vector at the surface of the radiation emitting device is calculated; that the path section between the point of exit and the point of the tissue, which is to be irradiated, is calculated; that the associated spatial volumes in the quality data of the tissue, for example the tumor tissue and/or the tissue in the vicinity of the tumor, are determined along the calculated path section; that the tissue types and their position and/or extension along the calculated path section are determined; that the radiation spectrum, which after transmission along the calculated path section exists at the point of the tissue, which is to be irradiated, is calculated; and that the dose rate at the point of the tissue, which is to be irradiated, is calculated from the radiation spectrum and the tissue type at the point of the tissue, which is to be irradiated.

This will be clarified by means of a concise embodiment as an example:

If at a specific location within the tissue G, the value of the dose rate D which reaches that location during the treatment, is desired, the course of calculation with the method according to the invention, may take place as follows, wherein in this example, the spectrum at the surface of the emitting device has to be known:

Firstly, the connecting vector between the isocentre I of a roentgen system XRS and the point G is determined. Then, the point of exit A of the connecting vector at the surface of the emitting device is calculated. Subsequently, the path section from A to G and the associated Voxels are calculated along this path section in the images, for example CT-images, which have been generated beforehand. Furthermore, the calculation or determination, respectively, of the tissue types and their respective position and/or extension along the path section from A to G or in the determined Voxels, respectively, is carried out. Furthermore, the radiation spectrum, for example roentgen spectrum, S is calculated, which is present at the endpoint G after transmission along the path section from A to G. The calculation of the absorbed dose rate D at point G is carried out from the radiation spectrum S and the tissue type at this point. Thereby, the physical effectiveness becomes known.

Preferably, further physical and/or biological and/or medical data may be generated and/or determined and/or provided, wherein the further physical and/or biological and/or medical data is being used for generating data for the tissue treatment, for example the tumor treatment, and/or is being provided for generating data for the tissue treatment, for example the tumor treatment.

For example, the RBE (relative biological effectiveness) may, if desired, be calculated and preferably be displayed, for example be shown, at each arbitrary location in the tissue as biological values and the probability of recurrence of the tumor (probability of recurrence) as medical values.

In order to solve the problem of comparability of the low-energy treatment with other treatment or therapeutic forms, such as for example an irradiation with linear accelerator, by means of the images as described further above, for example by means of CT-pictures, x-ray images or roentgenograms, those areas or the volume, for example by means of the further above mentioned Hounsfield-scale, in which the same treatment effectiveness is guaranteed by the low-energy system compared to other treatment forms, may additionally be calculate and subsequently shown in the image for information purpose for the user. For example, the so called "sphere of equivalence" may be envisioned. This is for example described in the article "Carsten Herskind, Jürgen Griebel, Uta Kraus-Tiefenbacher, Frederik Wenz—Sphere of Equivalence—a novel Target volume concept for intraoperative radiotherapy using low-energy X rays—in Int. J. Radiation Oncology Biol. Phys. Vol. 72 No. 5, pp 1575-1581 from 2008", the disclosure of which is incorporated into the description of the present invention by reference. These sphere of equivalence values may preferably be depicted in the image, for example in the CT-image or x-ray image.

In a preferred embodiment, the determined and/or calculated data and/or data for the tissue treatment, for example the tumor treatment, may visually be displayed on a display screen.

In particular, it may be provided, that the physical data of the radiation source and/or the physical property data of the determined tissue in connection with the radiation of the radiation source and/or the further physical and/or biological and/or medical data are visually displayed together with, in particular shown in, quality data of the tissue, for example the tumor tissue and/or the tissue in the vicinity of the tumor.

With the method according to the invention as described above, it, in particular, becomes possible to directly, visually illustrate the required data for planning the tissue treatment, in particular the tumor treatment, with the low-energy irradiation system on a display screen together with or shown in CT-images, x-ray images or roentgenograms of the tissue, for example the tumor tissue, with the tissue vicinity. The data, which is shown in the images, may provide the different users with important information regarding the physical/biological/medical effectiveness of the system and/or the treatment, which would otherwise cumbersomely have to be calculated by the user himself.

With the method according to the invention, the dose rate in the tissue can not only be calculated. This data may rather also be shown in an image of the tissue. In addition, also further biological/medical data/information can be calculated and also shown in the image.

The method according to the invention is based on the knowledge of the physical properties of the radiation of the low-energy irradiation system, for example the spectrum, and the physical property of different tissue types in connection with the radiation of the low-energy irradiation system and/or with soft x-rays, that means the energy dependent absorption behaviour and the like of tissue with x-radiation up to 100 keV, in particular up to 50 keV. Furthermore, the method is also based, in particular, on the knowledge of the image, for example the CT-picture or the roentgen picture, of the affected tissue vicinity, for example the tumor vicinity, with association of the gray levels of the picture pixels in the image to respective tissue types, for example on the basis of the Hounsfield scale.

A calculation in 3D is not necessarily mandatory. In general, a sectional view in 2D is also sufficient.

With sufficiently homogenous tissue, for example in case of a breast-only treatment, the method does not necessarily have to posses the ability of calculating heterogeneous tissue. In that case, the calculation of homogenous tissue would be sufficient.

According to a further aspect, a computer program is provided, which, if it is executed on a data processing device or unit or is loaded into such a device or unit, interacts such that the method according to the invention as described above, is executed on the data processing unit.

The computer program preferably is one for a low-energy irradiation system with calculation and display of the physical and/or biological and/or medical effectiveness of the system.

BRIEF DESCRIPTION OF THE DRAWINGS

Hereinafter, the invention will be explained more closely by means of embodiments with reference to the attached figures. Wherein.

DETAILED DESCRIPTION OF THE INVENTION

Figure 1:
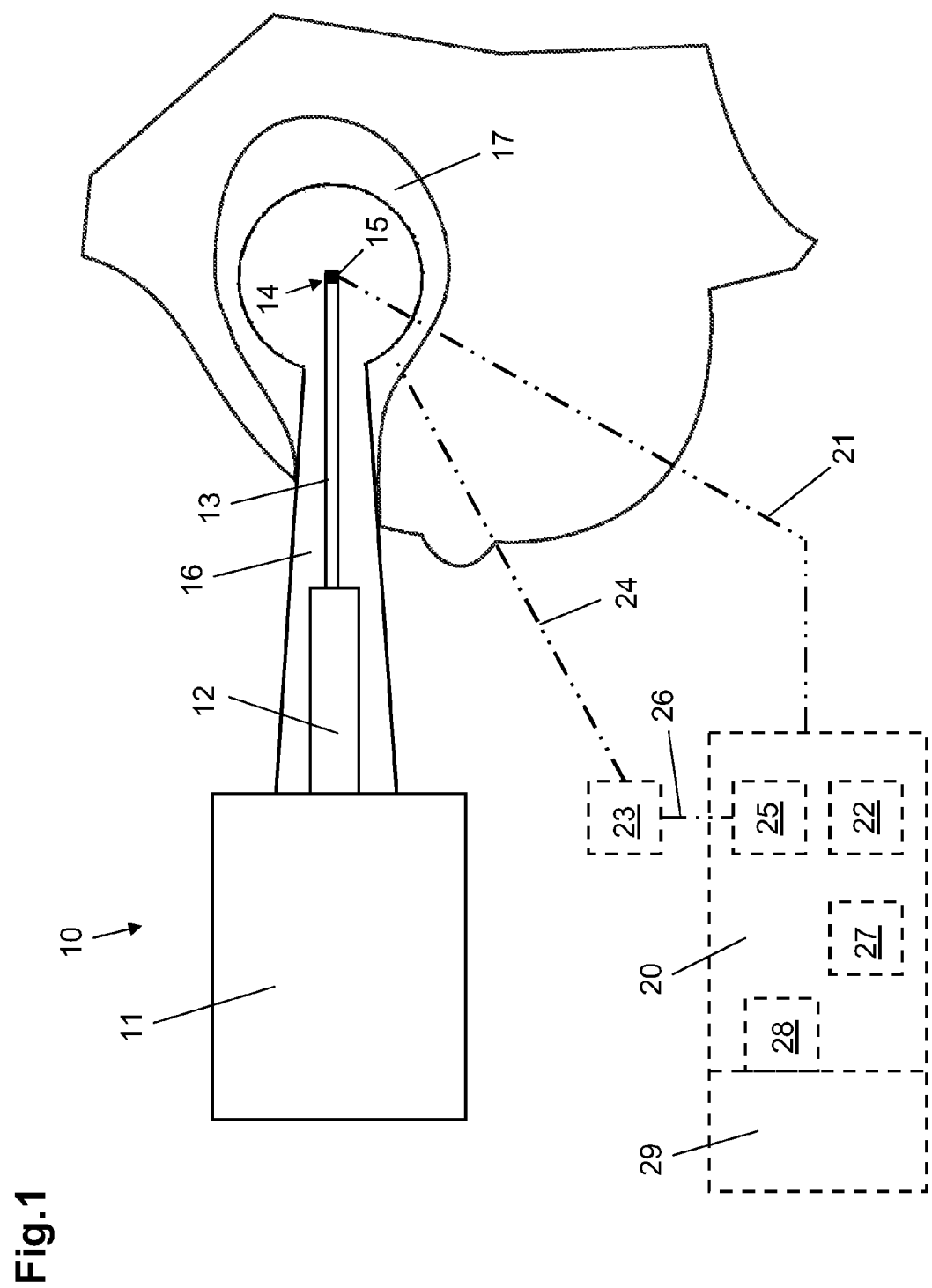
FIG. 1 shows, in schematic depiction, a low-energy irradiation appliance with which a method according to the invention for generating and/or providing data for an intraoperative tumor treatment can be carried out.

In FIG. 1 a low-energy irradiation appliance 10 is shown, which can be used for intraoperative irradiation of tissue after a breast tumor excision.

The low-energy irradiation appliance 10 has an arrangement 11 for generating an electron beam and an adjacent beam deflector 12. Furthermore a guiding device 13 for guiding the generated electron beam to a radiation source 14 is provided. The radiation source 14, which may have a gold target, generates a low-energy soft radiation, for example with a spectrum of from 0 to maximal radiation energy of 100 keV, in particular 50 keV. The radiation, which is generated by the radiation source 14, can be directed onto a tissue, which is to be irradiated, via an emitting device. Therein, the radiation can be released in a targeted fashion into the predefined tissue. For the targeted positioning of the radiation source 14 in the tumor bed or at the place of irradiation, as the case may be, applicator equipment 16 is provided, which is a balloon applicator in the depicted example.

The irradiation appliance 10 is supposed to serve for irradiating tissue 17 in the tumor vicinity during a breast irradiation. Firstly, the tumor is excised by surgery. Subsequently, the applicator equipment 16 is introduced at the irradiation place. Subsequently, the radiation source 14 is inserted into the applicator equipment 16, wherein the radiation source 14 can be positioned precisely by means of the applicator equipment 16.

The generating and providing of required data for the tumor treatment is effected with the method according to the invention, the course of which will be explained hereinafter in detail. For a better understanding, those components in the figure, which relate to the course of the method, are shown with dashed lines.

According to the present invention, a method of generating and/or providing data for a tumor treatment by means of the low-energy irradiation appliance 10 is provided. A processing unit 20 is provided for carrying out the method.

Physical data of the radiation source 14 is determined directly from leaving the emitting device 15. For example, it may be provided for this purpose, that the spectrum of the radiation source 14 is determined directly from leaving the emitting device 15 as physical data of the radiation source 14, which is clarified by the connecting line 21. The values of the spectrum or the spectra, respectively, may preferably be generated by means of appropriate measurements, the results of which are preferably stored in a file or data base. The file and/or data base is stored in a storage device 22, which the method or the processing unit 20, whereon the method is carried out, as the case may be, accesses or may access.

Furthermore, quality data of the tissue 17 in the tumor vicinity is determined. It may for example be provided, that the quality data of the tissue 17 in the vicinity of the tumor is generated by means of a device 23 for carrying out an image-providing method, which is clarified by the connecting line 24. For example, appropriate images, such as CT-images, x-ray images and the like, may be generated by means of device 23. In order to, preferably automatically, determine the type of the tissue 17 in the vicinity of the tumor, the images, for example CT-pictures or x-ray pictures, which have been taken beforehand, may for example be used. With the method according to the invention, for example, first an image of the tissue 17 in the vicinity of the tumor may be generated by means of an image-providing method. The thus generated image is then transmitted to an analysis device 25 within the processing unit 20, which is clarified by the connecting line 26, and is analysed in the analysis device 25 by means of an analysis method, for example with regards to the respective gray values. In the processing unit 20 the tissue type is then determined from the determined gray values and is provided in form of or as quality data.

Furthermore, physical property data of the determined tissue in connection with the radiation of the radiation source 14 is determined. Preferably, the mass-energy-absorption-coefficient is determined for this purpose.

In particular, it is provided, that for different tissue types, the mass-energy-absorption-coefficient dependent of the energy $[\mu/\rho(E)]$ {tissue type} in the soft radiation range, for example X-ray range, is known. It may, for example, be provided, that the mass-energy-adsorption-coefficients for different tissue types are or have been stored in a file or data base. The file and/or data base is preferably stored in a storage device 27, which the method or the processing unit 20, whereon the method is carried out, as the case may be, accesses or may access.

Subsequently, the data 28 for the tumor treatment is generated from the determined data and/or the determined data is provided for generating data for the tumor treatment. Preferably, the dose rate for the tissue, which is to be irradiated, may, in particular automatically, be calculated from the determined data.

The determined and/or calculated data and/or the data for the tumor treatment are visually illustrated on a display screen 29. In particular, it may be provided, that the physical data of the radiation source 14 and/or the physical property data of the determined tissue in connection with the radiation of the radiation source 14 and/or further physical and/or biological and/or medical data is visually illustrated together with, in particular shown in, the quality data of the tissue in the vicinity of the tumor.

Figure 2:
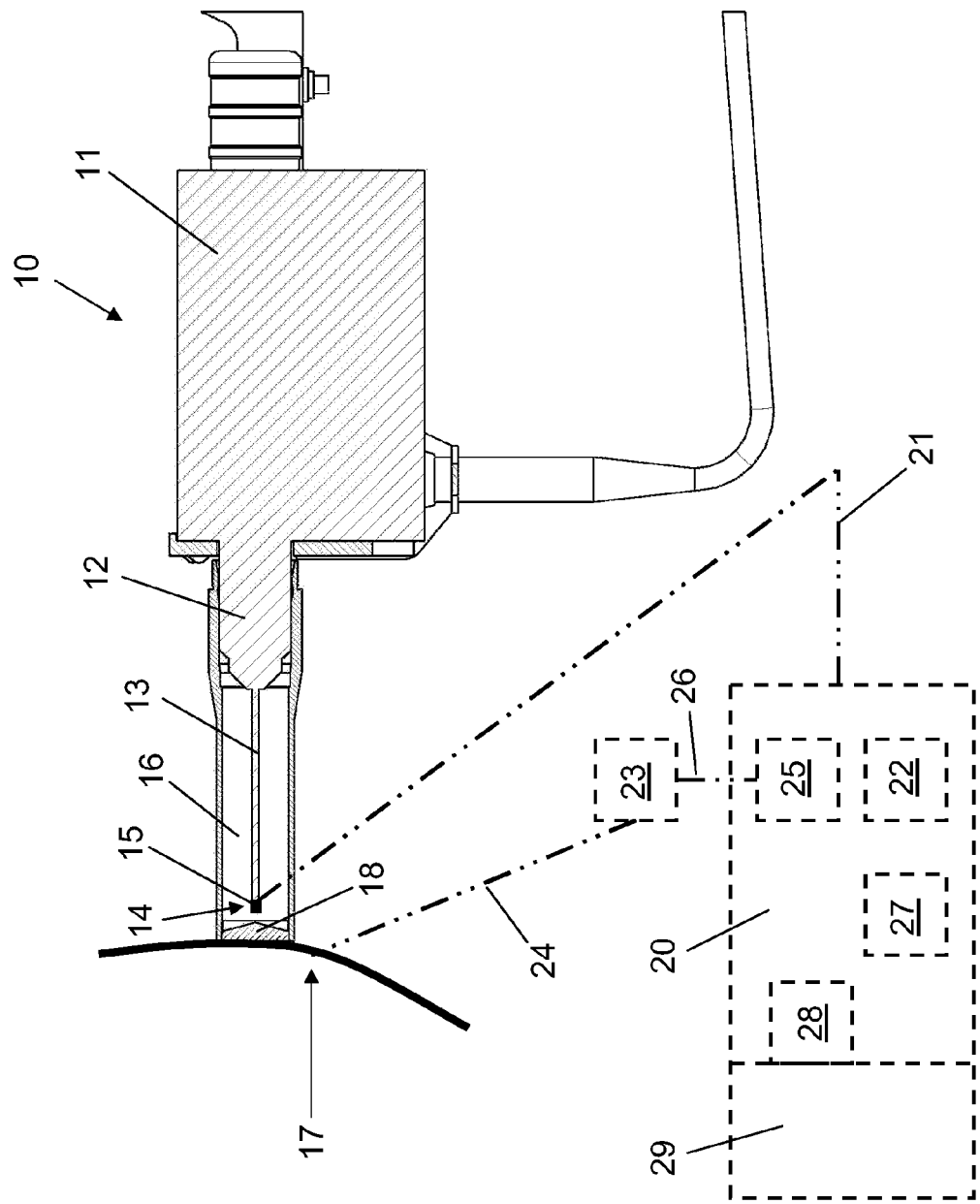
FIG. 2 shows, in schematic depiction, a low-energy irradiation appliance with which a method according to the invention for generating and/or providing data for a tissue treatment at the surface can be carried out.

In FIG. 2 a low-energy irradiation appliance 10 is depicted, which is used for irradiation of tissue at the body surface.

The low-energy irradiation appliance 10 has an arrangement 11 for generating an electron beam and an adjacent beam deflector 12. Furthermore, a guiding device 13 for guiding the generated electron beam to a radiation source 14 is provided. The radiation source 14, which may for example have a gold target, generates a low-energy soft radiation, for example with a spectrum of from 0 to maximal radiation energy of 100 keV, in particular 50 keV. Via an emitting device 15, the radiation, which is generated by the radiation source 14, can be directed onto a tissue, which is to be irradiated. Therein, the radiation can be released in a targeted fashion into the predefined tissue.

As further shown in FIG. 2, applicator equipment 16 is provided, which is a surface applicator, so that an irradiation of tissue 17 may be carried out also outside of the body, also independent of a tumor surgery. In the embodiment according FIG. 2 the radiation is not introduced intraoperatively, as was indicated in connection with FIG. 1. The radiation is rather applied to the surface, which is to be irradiated. In order to be able to generate different radiation characteristics with the applicator equipment 16, for example to be able to irradiate in different depths in a tissue, which is to be irradiated, the applicator equipment 16 of the embodiment, which is depicted in FIG. 2, has an element 18 for influencing the ray. The element 18 for influencing the ray is preferably provided as a lens for changing the ray characteristics. The element 18 is preferably exchangeably, that means detachably, arranged on the applicator equipment 16. The radiation is applied to the tissue surface 17, which is to be irradiated, from the radiation source 14 via the ray influencing element 18.

The embodiment which is shown in FIG. 2 and which has been described above, is, for example, also suitable for irradiation of surface lesions or tumors, in particular on the skin or on the surface of organs.

The generating and providing of the required data for the tissue treatment again is effected with the method according to the invention, the course of which will be explained hereinafter in detail. For a better understanding, also in FIG. 2, those components in the figure, which relate to the course of the method, are shown with dashed lines.

According to the present invention, a method of generating and/or providing data for a tumor treatment by means of the low-energy irradiation appliance 10 is provided. A processing unit 20 is provided for carrying out the method.

Physical data of the radiation source 14 is determined directly from leaving the emitting device 15. For example, it may be provided for this purpose, that the spectrum of the radiation source 14 is determined directly from leaving the emitting device 15 as physical data of the radiation source 14, which is clarified by the connecting line 21. The values of the spectrum or the spectra, respectively, may preferably be generated by means of appropriate measurements, the results of which preferably are stored in a file or data base. The file and/or data base is stored in a storage device 22, which the method or the processing unit 20, whereon the method is carried out, as the case may be, accesses or may access.

Furthermore, quality data of the tissue 17 in the tumor vicinity is determined. It may for example be provided, that the quality data of the tissue 17 in the vicinity of the tumor is generated by means of a device 23 for carrying out an image-providing method, which is clarified by the connecting line 24. For example, appropriate images, such as CT-images, x-ray images and the like, may be generated by means of the device 23. In order to, preferably automatically, determine the type of the tissue 17 in the vicinity of the tumor, the images, for example CT-pictures or x-ray pictures, which have been taken beforehand, may for example be used. With the method according to the invention, for example, first an image of the tissue 17 in the vicinity of the tumor may be generated by means of an image-providing method. The thus generated image is then transmitted to an analysis device 25 within the processing unit 20, which is clarified by the connecting line 26, and is analysed in the analysis device 25 by means of an analysis method, for example with regards to the respective gray values. In the processing unit 20, the tissue type is then determined from the determined gray values and is provided in form of or as quality data.

Furthermore, physical property data of the determined tissue in connection with the radiation of the radiation source 14 is determined. Preferably, the mass-energy-absorption-coefficient is determined for this purpose. In particular, it is provided, that for different tissue types, the mass-energy-absorption-coefficient dependent of the energy $[\mu/\rho(E)]$ {tissue type} in the soft radiation range, for example X-ray range, is known. It may, for example, be provided, that the mass-energy-adsorption-coefficients for different tissue types are or have been stored, respectively, in a file or data base. The file and/or data base is preferably stored in a storage device 27, which the method or the processing unit 20, whereon the method is carried out, as the case may be, accesses or may access.

Subsequently, the data 28 for the tumor treatment is generated from the determined data and/or the determined data is provided for generating data for the tumor treatment. Preferably, the dose rate for the tissue, which is to be irradiated, may, in particular automatically, be calculated from the determined data.

The determined and/or calculated data and/or the data for the tumor treatment are visually illustrated on a display screen 29. In particular, it may be provided, that the physical data of the radiation source 14 and/or the physical property data of the determined tissue in connection with the radiation of the radiation source 14 and/or further physical and/or biological and/or medical data is visually illustrated together with, in particular shown in, the quality data of the tissue in the vicinity of the tumor.

Figure 3:
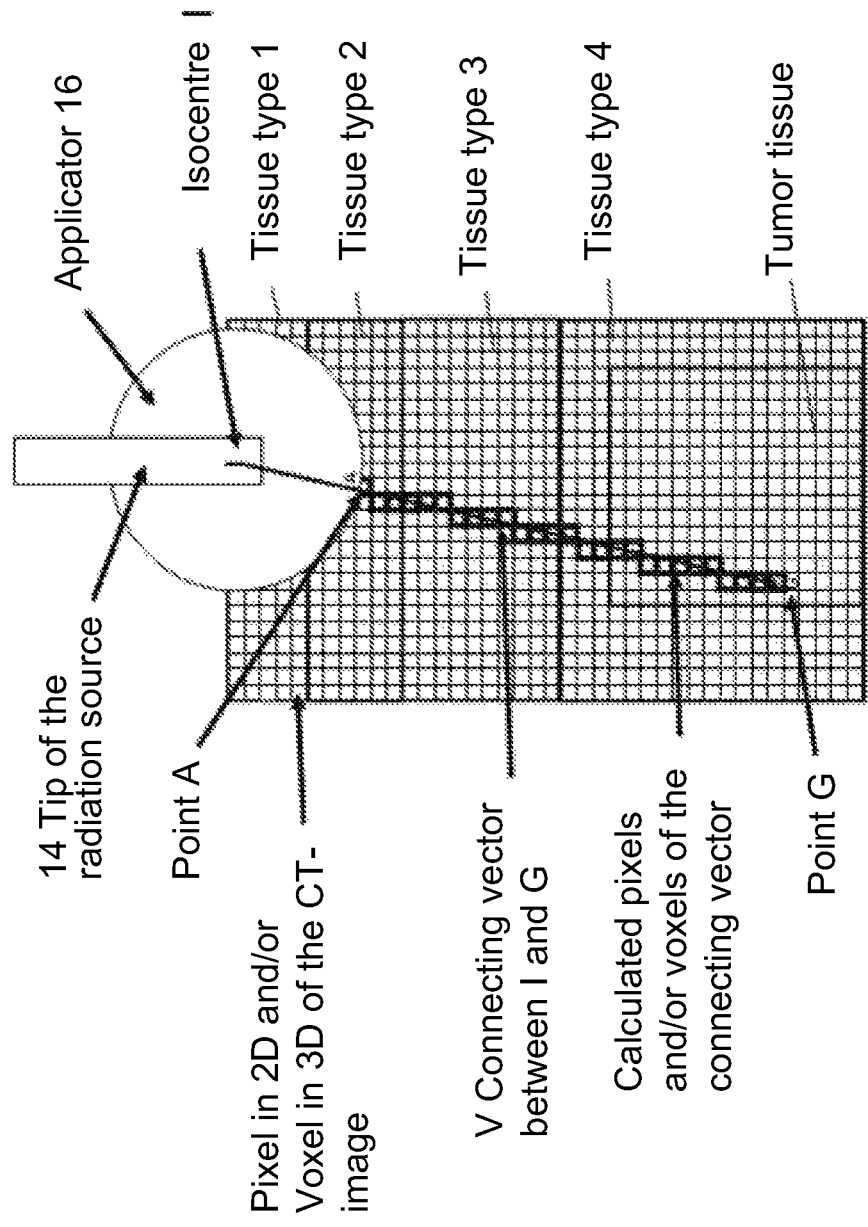
FIG. 3 shows, in schematic depiction, how the dose rate for a tissue, which is to be irradiated, can be calculated at a specific point G.

In FIG. 3 it is schematically shown, how the dose rate for tissue, which is to be irradiated, can be calculated at a specific point G. If at a specific point G in the tissue the value of the dose rate, which reaches that point during treatment is required or desired, it can now easily be calculated by means of the method according to the present invention.

If at a specific place in the tissue G, which may be located in a tumor tissue or in the surrounding area of the tumor tissue, the value of the dose rate, which reaches that place during a treatment, is desired, the course of calculation with the method according to the present invention, may be carried out as follows, wherein in this example, the spectrum at the surface of the emitting device has to be known.

Firstly, the connecting vector V between the isocentre I in the area of the tip of the radiation source 14—here an x-ray source—, which is located within an applicator equipment 16, and the point G is determined. Then the point of exit A of the connecting vector V at the surface of the emitting device, which in the present example is applicator equipment, is calculated. Subsequently, the path section from A to G through different tissue types 1, 2, 3 and 4 and the associated Voxels are calculated along this path section in the images, for example CT-images, which have been generated beforehand. Furthermore, the calculation or determination, respectively, of the tissue types 1, 2, 3 and 4 and their respective position and/or extension along the path section from A to G and/or in the determined Voxels is carried out. Furthermore, the radiation spectrum, for example roentgen spectrum, is calculated, which is present at the endpoint G after transmission along the path section from A to G. The calculation of the absorbed dose rate D at point G is carried out from the radiation spectrum S and the tissue type at this point. Thereby, the physical effectiveness becomes known.

REFERENCE NUMBERS 10 low-energy irradiation appliance
11 arrangement for generating an electron beam
12 ray deflector
13 guiding device for guiding the electron beam
14 radiation source
15 emitting device
16 applicator equipment
17 tissue in the vicinity of a tumor/tissue to be irradiated
18 element for influencing ray
20 processing unit
21 determining the spectrum of the radiation source
22 storage device with physical data of the radiation source
23 equipment for carrying out an image-providing method
24 generating of quality data of the tissue
25 analysis device
26 transmission of quality data
27 storage device with mass-energy-absorption-coefficients of different tissue types
28 data for tumor treatment
29 display screen

The invention claimed is:

1. Method for generating or providing data for a tissue treatment by means of a low-energy irradiation device, wherein the low-energy irradiation device has an irradiation source for generating soft radiation, preferably of a radiation with a spectrum of 0 to a maximal ray energy of 100 keV, in particular a radiation with a spectrum of 0 to a maximal radiation energy of 50 keV and an emitting device for emitting the irradiation to a tissue which is to be irradiated, characterized by the following steps:
    physical data of the irradiation source is determined directly upon leaving the emitting device;
    constitutional data of the tissue is determined;
    physical property data of the determined tissue is determined in connection with the irradiation of the irradiation source;
    data for the tissue treatment is generated from the determined data or the determined data is provided for generating data for the tissue treatment.

2. Method according to claim 1, characterized in that the spectrum of the radiation source directly upon leaving the emitting device, is determined as physical data of the radiation device.

3. Method according to claim 1, characterized in that the constitutional data of the tissue are determined by means of an image-providing method.

4. Method according to claim 1, characterized in that the mass-energy-absorption-coefficient is determined as physical property data of the determined tissue in connection with the radiation of the radiation source.

5. Method according to claim 1, characterized in that the dose-power for the tissue, which is to be irradiated, is determined from the determined data.

6. Method according to claim 5, characterized in that for calculation of the dose-power
    the connecting vector between the isocentre of the radiation emitting device and the point of the tissue, which is to be irradiated, is determined;
    that the exit point of the connecting vector at the surface of the radiation emitting device is calculated;
    that the distance between the exit point and the point of the tissue which is to be irradiated is calculated;
    that the associated spatial volumes in the constitutional data of the tissue is determined along the calculated distance;
    that the kinds of tissue and their position and/or extension along the calculated distance are determined;
    that the radiation spectrum, which after performed transmission along the calculated distance exists at the point of the tissue which is to be irradiated, is calculated; and
    that the dose-power at the point of the tissue, which is to be irradiated, is calculated from the radiation spectrum and the kind of tissue at the point of the tissue, which is to be irradiated.

7. Method according to claim 1, characterized in that further physical and/or biological and/or medical data may be generated and/or determined and/or provided and in that the further physical and/or biological and/or medical data is being used for generating data for the tissue treatment and/or is being provided for generating data for the tissue treatment, for example the tumor treatment.

8. Method according to claim 1, characterized in that the determined data and/or data for the tissue treatment are visually displayed on a display screen.

9. Method according to claim 8, characterized in that the physical data of the radiation source and/or the physical properties of the determined tissue in connection with the radiation of the radiation source and/or the further physical and/or biological and/or medical data together with constitutional data of the tissue, in particular blend in therein, are visually displayed.

10. Computer program product, which, if it is executed on a data processing device or is loaded in such a device, interacts with the data processing device such that on the data processing unit, the method according to claim 1 is executed.

* * * * *